United States Patent [19]

Ladewig

[11] Patent Number: 4,674,136
[45] Date of Patent: Jun. 23, 1987

[54] SAFETY MASK CONSTRUCTION

[76] Inventor: Christopher G. Ladewig, 26 Matteson St., Coventry, R.I. 02816

[21] Appl. No.: 862,841

[22] Filed: May 12, 1986

[51] Int. Cl.⁴ .............................................. A61F 9/02
[52] U.S. Cl. .......................................... 2/428; 2/439; 2/447; 2/450
[58] Field of Search ...................... 2/9, 174, 410, 421, 2/424, 428, 439, 206, 447, 450; 128/201.25, 206.13, 206.24, 207.11

[56] References Cited

U.S. PATENT DOCUMENTS

| | | | |
|---|---|---|---|
| 1,364,104 | 1/1921 | Geer | 128/206.24 |
| 1,491,674 | 4/1924 | Coletti | 128/206.13 |
| 1,813,915 | 7/1931 | Cover | 128/201.25 |
| 2,811,967 | 11/1957 | Stampe | 128/201.25 X |
| 3,308,816 | 3/1967 | Franklin et al. | 128/207.11 |
| 3,545,436 | 12/1970 | Holloway | 128/206.24 |
| 3,828,366 | 8/1974 | Conrad et al. | 2/174 |
| 4,136,688 | 1/1979 | Gorman | 128/201.25 |
| 4,157,090 | 6/1979 | Phillips | 128/207.11 |
| 4,271,538 | 6/1981 | Montesi | 2/439 |

Primary Examiner—Louis K. Rimrodt
Attorney, Agent, or Firm—Salter & Michaelson

[57] ABSTRACT

A safety mask construction comprises a substantially rigid face portion which is receivable over a portion of the face of a wearer and a pair of substantially rigid arm portions which extend rearwardly and inwardly from opposite sides of the face portion for engagement with the rear and upper rear portions of the head of the wearer. The arm portions are preferably hingeably attached to the face portion and biased toward inwardly hinged positions so that when the safety mask is mounted on the head of the wearer, they resiliently embrace the head to retain the face portion in proper orientation thereon.

6 Claims, 5 Drawing Figures

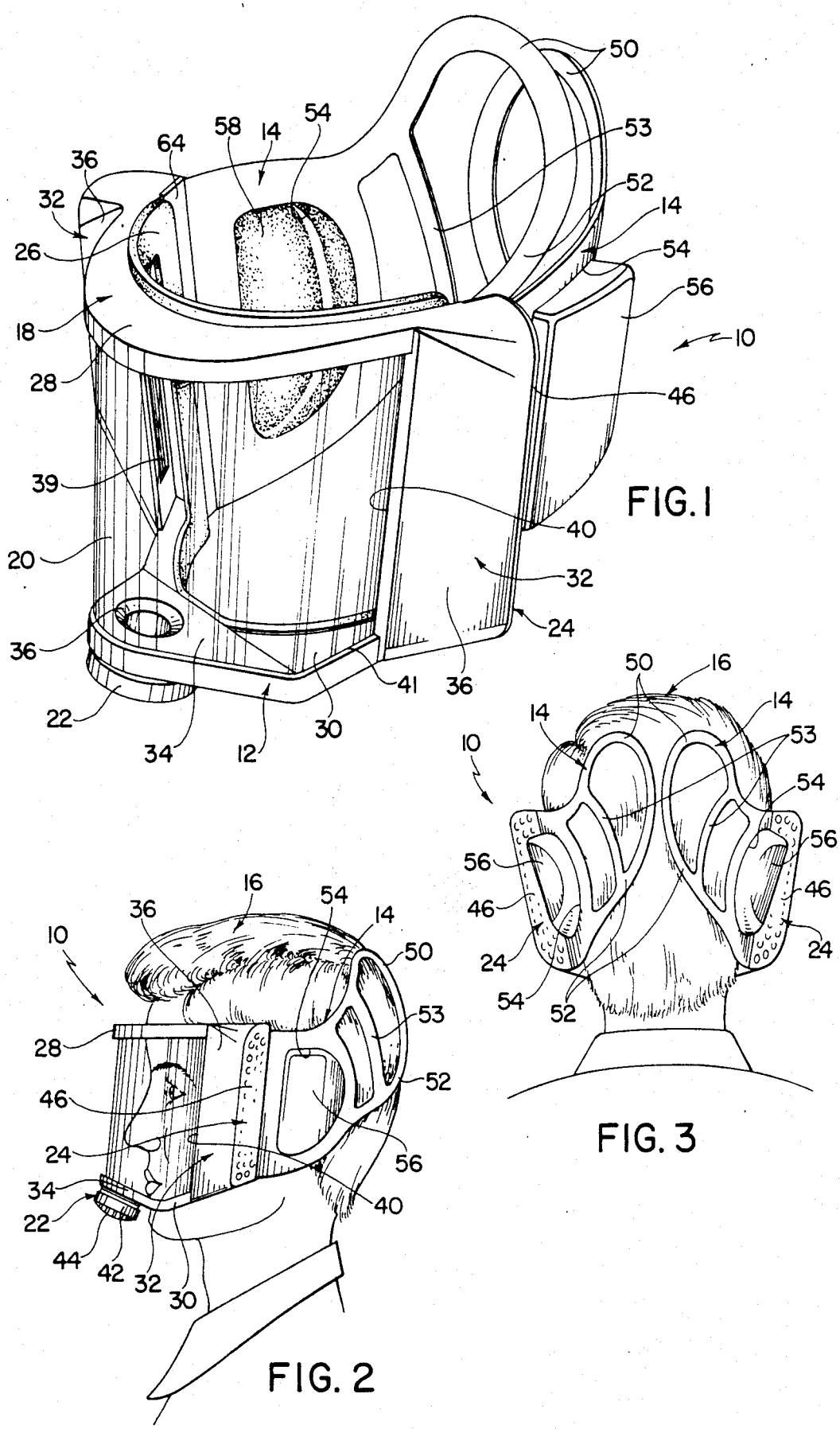

SAFETY MASK CONSTRUCTION

BACKGROUND AND SUMMARY OF THE INVENTION

The instant invention relates to safety equipment and more particularly to a safety mask construction which is adapted to be effectively and comfortably secured on the head of a wearer.

A variety of different types of safety masks have been heretofore available for providing respiratory protection and/or face and eye protection for persons who are exposed to various types of hazardous environments and conditions. In this regard, most of the heretofore available safety mask constructions have generally comprised a face portion which is adapted to be received in covering relation over a portion of the face of a wearer and a plurality of flexible straps which extend from the face portion and are receivable around the rear portion of the head for retaining the face portion in proper orientation on the head. It has been found, however, that in most instances, due to the rounded configuration of the human head, the use of flexible straps to secure the face portion of a safety mask on the head can be less than entirely effective. Specifically, it has been found that when a safety mask is constructed so that it includes flexible straps which are adapted to extend around the central rear portion of the head of a wearer, the straps tend to either slide downwardly so that they cause discomfort to the ears of the wearer or they tend to slide upwardly toward the tope of the head so that they become loosened and fail to effectively retain the face portion of the mask on the head without allowing it to sag. Further, it has been found that while these problems are generally characteristic of most of the heretofore available safety mask constructions which include flexible straps, they are compounded when the face portions of masks of this type include full face shields and/or respiratory elements which add weight thereto. Specifically, it has been found that when a safety mask of this type includes a relatively heavy face portion, the straps of the mask tend to slide upwardly or downwardly on the head even more quickly; and, as a result, the face portion of the mask tends to slide downwardly so that it is repositioned in an improper orientation on the face of the wearer. This has obvious disadvantages when a mask is adapted to provide respiratory protection for a wearer, since it can allow air to leak in around the sides of the mask; but, in any event, when the face portion of a mask slides downwardly on the face of a wearer, it inherently increases wearer discomfort.

The devices disclosed in the U.S. patents to GEER U.S. Pat. No. 1,364,104; COLETTI U.S. Pat. No. 1,491,674; COVER U.S. Pat. No. 1,813,915; STAMPE U.S. Pat. No. 2,811,967; FRANKLIN ET AL U.S. Pat. No. 3,308,816; HOLLOWAY U.S. Pat. No. 3,545,436; GORMAN U.S. Pat. No. 4,136,688; and PHILLIPS U.S. Pat. No. 4,157,090 are generally exemplary of the wide variety of different types of safety mask constructions which have been heretofore available and represent the closest prior art to the instant invention of which the applicant is aware. However, while the devices disclosed in these references are believed to be generally representative of the state of the art with respect to safety mask constructions, they nevertheless fail to teach a safety mask construction which is adapted to be effectively retained on the head of a wearer without sacrificing wearer comfort. More specifically, they fail to teach a safety mask construction comprising a face mask portion and means for securing the face mask portion on the head of a wearer, wherein the face mask portion is not prone to sagging and wherein the securing means is nevertheless adapted for maximum wearer comfort. For these reasons, the above references fail to anticipate the highly desirable and novel structural features of the safety mask construction of the instant invention; and as a result, they are believed to be of only general interest.

The instant invention provides a safety mask construction which is adapted to be easily mounted on the head of a wearer so that it is effectively and comfortably retained thereon, and therefore the instant invention effectively overcomes the disadvantages of many of the heretofore available safety masks. Specifically, the safety mask construction of the instant invention comprises a substantially rigid face portion which is dimensioned and configured to be received in covering relation over at least a portion of the face of a wearer and a pair of substantially rigid arm portions which normally extend rearwardly and together from opposite side extremities of the face portion. The arm portions of the mask are constructed so that they are resiliently separable from each other for installing the safety mask on the head of a wearer, and each of the arm portions includes an upper portion which is constructed so that it embraces a portion of the head of the wearer which faces rearwardly and upwardly when the mask is installed thereon, and a lower portion which is constructed so that it embraces a portion of the head which faces rearwardly but not upwardly when the mask is installed thereon. In other words, the arm portions embrace the rearmost portions of the head which inherently face generally rearwardly when the head is in an upright disposition, and they also embrace the upper rear portions of the head. In the preferred embodiment of the safety mask construction, the arms are hingeably attached to opposite side extremities of the face portion, and they are resiliently biased toward inwardly hinged positions so that they are positionable in resiliently biased engagement with the rear and upper rear portions of the head of the wearer, and preferably the arms are constructed so that they terminate in closely adjacent relation on the rear portion of the head when the mask is installed thereon. The face portion of the safety mask is preferably dimensioned and configured to cover substantially the entire face of a wearer, although it could also be constructed so that it only covers a portion of the face, such as the nose and mouth portion or the eye portion. Further, the face mask is preferably constructed so that it is receivable in substantially sealed engagement with the face, and it preferably comprises respirator means for filtering air which is introduced into the face portion. In addition, the face portion is preferably constructed so that when it is received on the face of a wearer, the side extremities of the face portion are positioned in front of the wearer's ears, and the safety mask preferably further comprises ear protector elements which are mounted on the arms so that they cover the ears of the wearer when the mask is mounted on the head.

Accordingly, it is seen that the safety mask construction of the instant invention is adapted to be effectively and comfortably worn on the head of a wearer. Specifically, the safety mask is constructed so that the upper portions of the arm portions thereof embrace portions of the head of a wearer which face rearwardly and upwardly and so that the lower portions of the arm portions thereof embrace rearmost portions of the head which face rearwardly but not upwardly. Accordingly, the arm portions of the safety mask tend to grasp the rear and upper rear portions of the head to prevent the face portion of the mask from sagging downwardly so that it is repositioned with respect to the face of the wearer. Further, since the face portion and the arm portions of the safety mask are made in substantially rigid constructions, and since the arm portions are biased toward inwardly hinged positions, the effectiveness with which the arm portions can grasp the rear portion of the head is further enhanced. Accordingly, the safety mask of the instant invention can be comfortably worn on the head, and the face portion of the mask can be effectively retained in proper orientation with the head, even when the face portion includes respirator elements and/or a full face shield.

Accordingly, it is a primary object of the instant invention to provide a safety mask construction which is adapted to be effectively and comfortably worn on the head of a wearer.

Another object of the instant invention is to provide a safety mask construction which comprises a pair of substantially rigid arm portions which are operative for grasping the rear and upper rear portions of the head of a wearer to secure the safety mask thereon.

Another object of the instant invention is to provide a safety mask construction wherein the face portion thereof is effectively securable in proper orientation on the head of a wearer.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 1 is a perspective view of the safety mask construction of the instant invention;

FIG. 2 is a side elevational view of the safety mask construction on the head of a wearer;

FIG. 3 is a rear elevational view of the mask on the head of a wearer;

DESCRIPTION OF THE INVENTION

Figure 4:
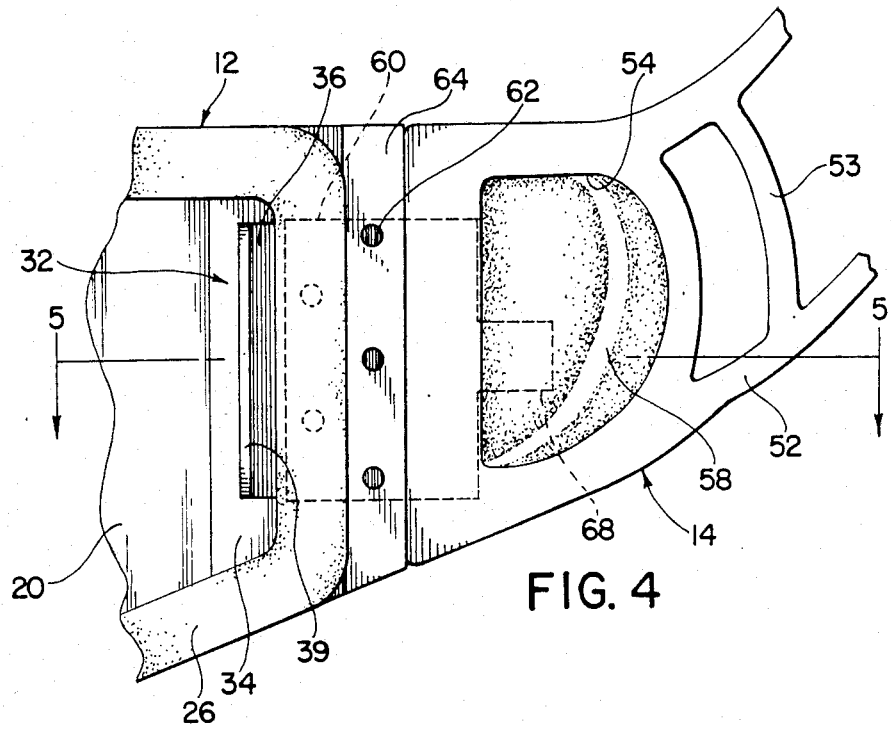
FIG. 4 is an elevational view of a portion of the inner side of the safety mask construction where one of the arm portions thereof is secured to the face portion.
Figure 5:
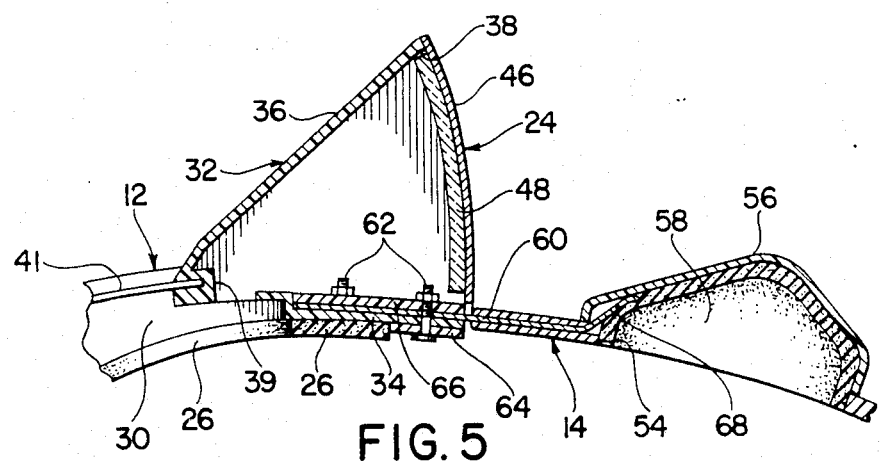
FIG. 5 is a sectional view taken along line 5—5 in FIG. 4.

Referring now to the drawings, the safety mask construction of the instant invention is illustrated in FIGS. 1 through 5 and generally indicated at 10 in FIGS. 1 through 3. The safety mask 10 comprises a substantially rigid face portion generally indicated at 12 and a pair of substantially rigid arm portions, each generally indicated at 14, which normally extend rearwardly and inwardly from opposite side extremities of the face portion 12. For use of the safety mask 10, it is assembled on the head of a wearer, such as the wearer generally indicated at 16 in FIGS. 2 and 3, so that the face portion 12 covers a portion of the face of the wearer 16 and so that the arm portions 14 embrace the rear and upper rear portions of the head of the wearer 16 to secure the mask 10 thereon.

The face portion 12 comprises a body portion generally indicated at 18 which is preferably injection molded from a self-skinning foam-plastic or some other similarly lightweight, strong, resilient material, a window element 20, an exhaust valve 22, a pair of filter assemblies generally indicated at 24, and an inner seal 26. The body portion 18 preferably comprises an arcuate upper frame member 28, a lower frame member 30 having an arcuate inner configuration and a pair of side frame members 32 which extend between the upper and lower frame members 28 and 30 and define the side extremities of the face portion 12. Accordingly, the upper and lower frame members 28 and 30 and the side frame members 32 cooperate to define a configuration in the body portion 18 which allows it to be received in closely adjacent relation with the peripheral portions of the face of the wearer 16. The lower frame member 30 includes a forwardly extending lip portion 34 through which an aperture 36 extends, and the exhaust valve 22 is assembled and secured on the outer side of the lip portion 34 so that it communicates with the interior of the face portion 12 through the aperture 36. As illustrated most clearly in FIGS. 1 and 5, the side portions 32 have generally rearwardly and outwardly flared, open V-shaped sectional configurations which are defined by inner walls 34 thereof which extend rearwardly from the inner surfaces of the upper and lower frame portions 28 and 30, respectively, and outer walls 36 which angularly diverge from the inner walls 34 in their rearward extents to define enlarged, substantially rearwardly facing openings 38. Formed in the forward portions of the inner walls 34 are elongated, substantially vertically disposed openings 39 which extend from the interior of the face portion 12 to the interiors of their respective side portions 32. The upper and lower frame portions 28 and 30, respectively, and the side frame portions 32 cooperate to define an opening 40 in the body portion 18 wherein the window element 20 is received, and a channel 41 is provided in the body portion 18 around the periphery of the opening 40, for receiving and retaining the window element 20.

The window element 20 is preferbly constructed of a suitable transparent plastic material and it is preferably dimensioned and configured to be received in the opening 40 with the peripheral edge portions of the window portion 20 received in the channel 42.

The exhaust valve 22 is preferably of conventional construction, and it preferably comprises a substantially circular outer housing 42 having a plurality of slots 44 in the terminal end thereof, and a substantially circular flexible diaphragm (not shown) which is received and secured in the interior of the housing 42 and which is operative for allowing gases to be passed outwardly through the exhaust valve 22 but for preventing substantial quantities of gases from being drawn inwardly therethrough.

The filter assemblies 24 are received in the rearwardly facing openings 38 in the side portions 32 and they each comprise an apertured outer cover plate 46 which is received in covering relation over the respective opening 38 thereof and a filter element 48 which preferably comprises a conventional filter medium, such as a fibrous sheet, and which is secured on the inner surface of its respective adjacent cover plate 46 so that it covers the apertures therein.

The seal 26 is preferably extruded from a relatively soft rubberized material, and it is secured on the inner surface of the body portion 18 so that it is receivable in engagement with the head of a wearer for providing a cushioned seal between the body portion 18 and the head of the wearer 16.

The arms 14 are attached to the face portion 12 and they are constructed and positioned so that when the face portion 12 is positioned in covering relation over the face, the arms 14 embrace the rear and upper rear portions of the head of the wearer 16 to secure the face portion 12 in proper orientation on the face of the wearer 16. More specifically, the arms 14 are attached to the side extremities of the face portion 12, and they are made in substantially rigid constructions wherein they normally extend arcuately rearwardly, upwardly, and inwardly from the face portion 12 and wherein they substantially conform to the configuration of the rear and upper rear portions of the head of the wearer 16. In this connection, as illustrated most clearly in FIGS. 2 and 3, the arms 14 each comprise an upper portion 50 which is positioned so that it is engageable with a portion of the head of the wearer 16 which faces rearwardly and upwardly when the face mask 10 is mounted on the head and the head is in a substantially upright disposition, a lower portion 52 which is engageable with a portion of the head which faces rearwardly but not upwardly when the face mask 10 is mounted on the head and the head is in an upright disposition and a terminal portion 52a. The terminal portions 52a extend between the rear end portions of the upper portions 50 and the lower portions 52, and they are disposed in closely adjacent relation to each other and embrace a portion of the head of a wearer 16 which faces predominanty rearwardly when the mask 10 is received on the head. Hence, the arms 14 are constructed and oriented so that they are able to grasp the rear and upper rear portions of the head of the wearer 16 in a manner which allows them to apply both rearward and upward retaining forces to the face portion 12 in order that the face portion 12 is effectively held in a properly oriented position wherein it covers the face of the wearer 16 and wherein the seal 26 is in sealed engagement therewith. The arms 14 are also preferably injection molded from a suitable plastic material, and they are made in substantially rigid constructions so that they can effectively embrace the rear portion of the head of the wearer 16 to apply the appropriate retaining forces to the face portion 12. Further, the arms preferably include rigid connector strips 53 which extend between the upper portions 50 and the lower portions at intermediate points in the extents thereof 52 for providing increased rigidity, although other constructions for the arms, such as constructions wherein they are formed without open areas between the upper and lower portions 50 and 52 are contemplated. Formed in the forward portions of the arms 14 are openings 54 which are oriented so that when the mask 10 is received on the head of the wearer 16, the ears of the wearer are received in the openings 54, and ear protector caps 56 having sound deadening liners 58 therein are received in the openings 54 so that the caps 56 project outwardly for covering the ears of the wearer 16 when the face mask 10 is received on the head of the wearer.

The arms 14 are preferably secured to the side extremities of the face portion 12 so that they are inwardly hingeable with respect thereto and so that the ends of the arms 14 are biased toward inwardly hinged positions to allow them to effectively embrace the head of the wearer 16. As illustrated in FIGS. 3 and 4, each of the arms 14 is preferably secured to the face portion 12 with a resilient spring plate 60 which is secured to the adjacent inner wall 34 with a pair of screws 62 and inner and outer reinforcing plates 64 and 66, respectively, which are preferably made of a rigid plastic material are provided for reinforcing the inner wall 24. Each of the spring plates 60 extends rearwardly from its respective side of the face portion 12 and is received in the forward portion of its respective adjacent arm 14, terminating in an outwardly extending foot 68 which is received in the adjacent ear cap 56 between the inner surface thereof and the inner liner 58 thereof. Accordingly, the arms 14 are actually hingeably attached to the face portion 12 by means of the spring plates 60, although the spring plates 60 also function to bias the arms 14 to positions wherein they are hinged inwardly and together. However, because the spring plates 60 are resiliently flexible, the arms 14 can nevertheless be hinged outwardly to allow the face mask 10 to be easily positioned on the head of the wearer 16. It should be pointed out, however, that other embodiments of the face mask construction of the instant invention which include arms which are integrally formed with the face portion but nevertheless biased inwardly and together are also contemplated.

It is see, therefore, that the instant invention provides an effective safety mask construction which is securable on the head of a wearer, such as the wearer 16, so that the face of the wearer 16 is protected from various hazards. In this connection, because the face mask 10 comprises a substantially rigid face portion 12 and a pair of substantially rigid arms 14 which are mounted on the face portion 12 so that they extend rearwardly and upwardly therefrom for embracing the rear and upper rear portions of the head of the wearer 16, the mask 10 can be effectively retained on the head of the wearer 16. Further, because the arms 14 embrace the rear and upper rear portions of the head of the wearer 16, they prevent the face portion 12 from sagging downwardly on the face of the wearer 16. During use of the safety mask 10, the exhaust valve 22 allows air to escape from the interior of the face portion 12 as the wearer 16 exhales; whereas the filter portions 24 function as respirators which filter air which is drawn inwardly therethrough into the interior of the face portion 12 as the wearer 16 inhales. The ear protector caps 56 provide ear protection for the wearer 16, and they are mounted on the arms 14 so that they are effectively positionable in covering relation over the ears of the wearer 16. The arms 14 are resiliently biased to inwardly hinged positions by means of the springs 60, although they are separable to allow the safety mask 10 to be installed on the head of a wearer and they can nevertheless effectively apply pressures to the rear portions of the head of the wearer 16 to firmly secure the face mask 10 thereon. Hence, it is seen that the safety mask construction of the instant invention has significant advantages over the heretofore available safety masks and that it therefore represents a significant advancement in the art of safety equipment which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A safety mask construction comprising a substantially rigid face portion which is dimensioned and configured to be received in covering relation over at least a portion of the face of a wearer of said mask and a pair of substantially rigid arm portions which normally extend rearwardly and together from opposite side extremities of said face portion, said arm portions being resiliently separable from each other for installing said safety mask on the head of said wearer and each having an upper portion which extends inwardly, rearwardly, and upwardly from an upper side portion of said face portion and embraces a portion of the head of said wearer which faces rearwardly and upwardly when said mask is installed on said head and said head is in an upright disposition in order to resist downward movement of said mask on said head a lower portion which is downwardly spaced from said upper portion and embraces a portion of said head which faces rearwardly but not upwardly when said mask is installed on said head and said head is in an upright disposition, and a terminal portion which extends between the respective upper and lower portions thereof, said terminal portions being disposed in closely adjacent relation and embracing portions of said head which face predominantly rearwardly when said mask is installed on said head and said head is in an upright disposition.

2. In the safety mask of claim 1, said arm portions embracing said head in resiliently biased engagement therewith when said safety mask is installed thereon.

3. In the safety mask of claim 1, said arm portions being hingeably attached to opposite side extremities of said face portion, said safety mask further comprising means for biasing said arm portions together.

4. In the safety mask of claim 1, said face portion being dimensioned and configured to cover substantially the entire face of said wearer and being positionable in substantially sealed engagement therewith, said face portion further comprising respirator means for filtering air which is introduced into said face portion.

5. In the safety mask of claim 1, said face portion being constructed so that the side extremities thereof are disposed in front of the ears of said wearer when said safety mask is installed on said head, said safety mask further comprising ear protector means mounted on said arm portions and positioned thereon so that they cover the ears of said wearer when said safety mask is mounted on said head.

6. In the safety mask of claim 5, said arm portions being hingeably attached to opposite side extremities of said face portion, said safety mask further comprising means for biasing said arm portions together and also for biasing said ear protector means into covering relation over said ears.

* * * * *